United States Patent
Stuart et al.

(10) Patent No.: US 9,812,035 B2
(45) Date of Patent: Nov. 7, 2017

(54) SYSTEM AND METHOD FOR DEMONSTRATING PLANNED AUTONOMOUS MANIPULATION OF AN ANATOMY

(71) Applicant: MAKO Surgical Corp., Ft. Lauderdale, FL (US)

(72) Inventors: John Michael Stuart, Rio Rancho, NM (US); Jerry A. Culp, Kalamazoo, MI (US); Jose Luis Moctezuma de la Barrera, Freiburg (DE)

(73) Assignee: MAKO SURGICAL CORP., Fort Lauderdale, FL (US)

( * ) Notice: Subject to any disclaimer, the term of this patent is extended or adjusted under 35 U.S.C. 154(b) by 0 days.

(21) Appl. No.: 15/158,909

(22) Filed: May 19, 2016

(65) Prior Publication Data

US 2016/0343273 A1 Nov. 24, 2016

Related U.S. Application Data

(60) Provisional application No. 62/163,654, filed on May 19, 2015.

(51) Int. Cl.
*G06F 19/00* (2011.01)
*G09B 23/28* (2006.01)
(Continued)

(52) U.S. Cl.
CPC ............. *G09B 23/28* (2013.01); *A61B 17/16* (2013.01); *A61B 34/30* (2016.02); *A61B 34/32* (2016.02);
(Continued)

(58) Field of Classification Search
CPC ......... G09B 23/28; A61B 34/30; A61B 34/32; A61B 34/77; A61B 17/16; B25J 9/1666; B25J 9/1676
See application file for complete search history.

(56) References Cited

U.S. PATENT DOCUMENTS

| 5,710,870 A | 1/1998 | Ohm et al. |
| 6,507,773 B2 | 1/2003 | Parker et al. |

(Continued)

OTHER PUBLICATIONS

International Search Report for PCT/US2016/033221; dated Aug. 29, 2016; 16 pages.
Neil Glossop et al.; Augmented Reality Laser Projection Device for Surgery; 7 pages; University of Western Ontario.

*Primary Examiner* — Ian Jen
(74) *Attorney, Agent, or Firm* — Howard & Howard Attorneys PLLC

(57) ABSTRACT

Surgical systems and methods of demonstrating planned autonomous manipulation of an anatomy by a tool of a robotic surgical system include generating manipulation parameters representing planned constraints on autonomous manipulation of a volume of the anatomy by the tool in a first mode and generating demonstrative parameters relating to the manipulation parameters and defined in relation to a surface of the anatomy. The demonstrative parameters are less invasive to the anatomy than the manipulation parameters. The tool is moved in accordance with the demonstrative parameters in a second mode thereby demonstrating planned constraints on autonomous manipulation of the anatomy in relation to the surface of the anatomy.

32 Claims, 8 Drawing Sheets

(51) Int. Cl.
| | |
|---|---|
| *B25J 9/16* | (2006.01) |
| *A61B 34/30* | (2016.01) |
| *A61B 34/32* | (2016.01) |
| *A61B 34/00* | (2016.01) |
| *A61B 17/16* | (2006.01) |
| *A61B 90/00* | (2016.01) |
| *A61B 34/10* | (2016.01) |

(52) U.S. Cl.
CPC ............ *A61B 34/77* (2016.02); *B25J 9/1666* (2013.01); *B25J 9/1676* (2013.01); *A61B 2034/107* (2016.02); *A61B 2034/303* (2016.02); *A61B 2090/062* (2016.02); *A61B 2090/08021* (2016.02)

(56) References Cited

U.S. PATENT DOCUMENTS

| | | |
|---|---|---|
| 8,761,931 B2 | 6/2014 | Halloran et al. |
| 9,119,655 B2 | 9/2015 | Bowling et al. |
| 9,381,085 B2 | 7/2016 | Axelson, Jr. et al. |
| 2012/0158011 A1* | 6/2012 | Sandhu .................. A61B 34/30 606/130 |
| 2013/0035690 A1* | 2/2013 | Mittelstadt ............. A61B 17/17 606/79 |
| 2014/0039517 A1* | 2/2014 | Bowling .................. B25J 13/00 606/130 |

* cited by examiner

SYSTEM AND METHOD FOR DEMONSTRATING PLANNED AUTONOMOUS MANIPULATION OF AN ANATOMY

CROSS-REFERENCE TO RELATED APPLICATION

This application claims priority to and the benefit of U.S. provisional patent application No. 62/163,654 filed May 19, 2015, the disclosure of which is hereby incorporated by reference in its entirety.

TECHNICAL FIELD

The present invention relates generally to a system and method for demonstrating planned autonomous manipulation of an anatomy.

BACKGROUND

Robotic surgical systems are increasingly utilized to perform surgical procedures on patients. The robotic surgical system typically includes a robotic device including a moveable arm having a free, distal end, which may be placed with a high degree of accuracy. A tool or end effector, which is applied to the surgical site, attaches to the free end of the arm. The operator is able to move the arm and thereby precisely position the tool at the surgical site to perform the procedure.

Operators often desire dynamic control of the tool in different manipulation modes during a surgical operation. For example, in some instances, the operator may desire a manual mode to control the tool manually for bulk manipulation of the anatomy. In other instances, the operator may desire to control the tool in an autonomous mode for automated and highly accurate manipulation of the anatomy.

In view of the efficiency and accuracy of autonomous manipulation, it is likely that autonomous manipulation will replace manual manipulation in the future. However, operators may be hesitant to commit to autonomous manipulation in the operating room. Many operators prefer manual manipulation because manual manipulation gives the operator the impression of having total control over the tool. Said differently, operators may hesitate to allow the robotic device to autonomously operate on the patient because of a perceived lack of control associated with autonomous manipulation.

SUMMARY

One embodiment of a robotic surgical system for manipulating an anatomy and demonstrating planned autonomous manipulation of the anatomy is provided. The robotic surgical system includes a tool configured to manipulate the anatomy. A controller is configured to generate manipulation parameters representing planned constraints on autonomous manipulation of a volume of the anatomy by the tool in a first mode. The controller generates demonstrative parameters relating to the manipulation parameters. The demonstrative parameters are defined in relation to a surface of the anatomy such that the demonstrative parameters are less invasive to the anatomy than the manipulation parameters. The controller is configured to instruct movement of the tool in accordance with the demonstrative parameters in a second mode thereby demonstrating planned constraints on autonomous manipulation of the anatomy in relation to the surface of the anatomy.

Another embodiment of a robotic surgical system for manipulating an anatomy and demonstrating planned autonomous manipulation of the anatomy is provided. The robotic surgical system includes an end effector configured to manipulate the anatomy and a demonstrative tool configured to interact with the anatomy. A controller is configured to generate manipulation parameters representing planned constraints on autonomous manipulation of a volume of the anatomy by the end effector in a first mode. The controller generates demonstrative parameters relating to the manipulation parameters. The demonstrative parameters are defined in relation to a surface of the anatomy such that the demonstrative parameters are less invasive to the anatomy than the manipulation parameters. The controller is configured to instruct movement of the demonstrative tool in accordance with the demonstrative parameters in a second mode thereby demonstrating planned constraints on autonomous manipulation of the anatomy in relation to the surface of the anatomy.

One embodiment of a method of demonstrating planned autonomous manipulation of an anatomy by a tool of a robotic surgical system is also provided. The method comprises generating manipulation parameters representing planned constraints on autonomous manipulation of a volume of the anatomy by the tool in a first mode. Demonstrative parameters relating to the manipulation parameters are generated. The demonstrative parameters are defined in relation to a surface of the anatomy such that the demonstrative parameters are less invasive to the anatomy than the manipulation parameters. The tool is autonomously moved in accordance with the demonstrative parameters in a second mode thereby demonstrating planned constraints on autonomous manipulation of the anatomy in relation to the surface of the anatomy.

Another embodiment of a method of demonstrating planned autonomous manipulation of an anatomy by an end effector of a robotic surgical system is also provided. The method comprises generating manipulation parameters representing planned constraints on autonomous manipulation of a volume of the anatomy by the end effector in a first mode. Demonstrative parameters relating to the manipulation parameters are generated. The demonstrative parameters are defined in relation to a surface of the anatomy such that the demonstrative parameters are less invasive to the anatomy than the manipulation parameters. A demonstrative tool is autonomously moved in accordance with the demonstrative parameters in a second mode thereby demonstrating planned constraints on autonomous manipulation of the anatomy in relation to the surface of the anatomy.

The system and method advantageously demonstrate planned autonomous manipulation in the second mode. Unlike the invasiveness of manipulation in the first mode, demonstration in the second mode is minimally or non-invasive as it is performed in relation to the surface of the anatomy. By autonomously moving the end effector or demonstrative tool in the second mode, the operator can visualize a representation of planned autonomous movement before committing to autonomous manipulation in the first mode. Thus, the second mode provides operators with a greater sense of control and confidence thereby alleviating operator hesitancy in using autonomous manipulation in the first mode.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. Overview

Referring to the Figures, wherein like numerals indicate like or corresponding parts throughout the several views, a system 10 and method for manipulating an anatomy of a patient 12 are shown throughout.

Figure 1:
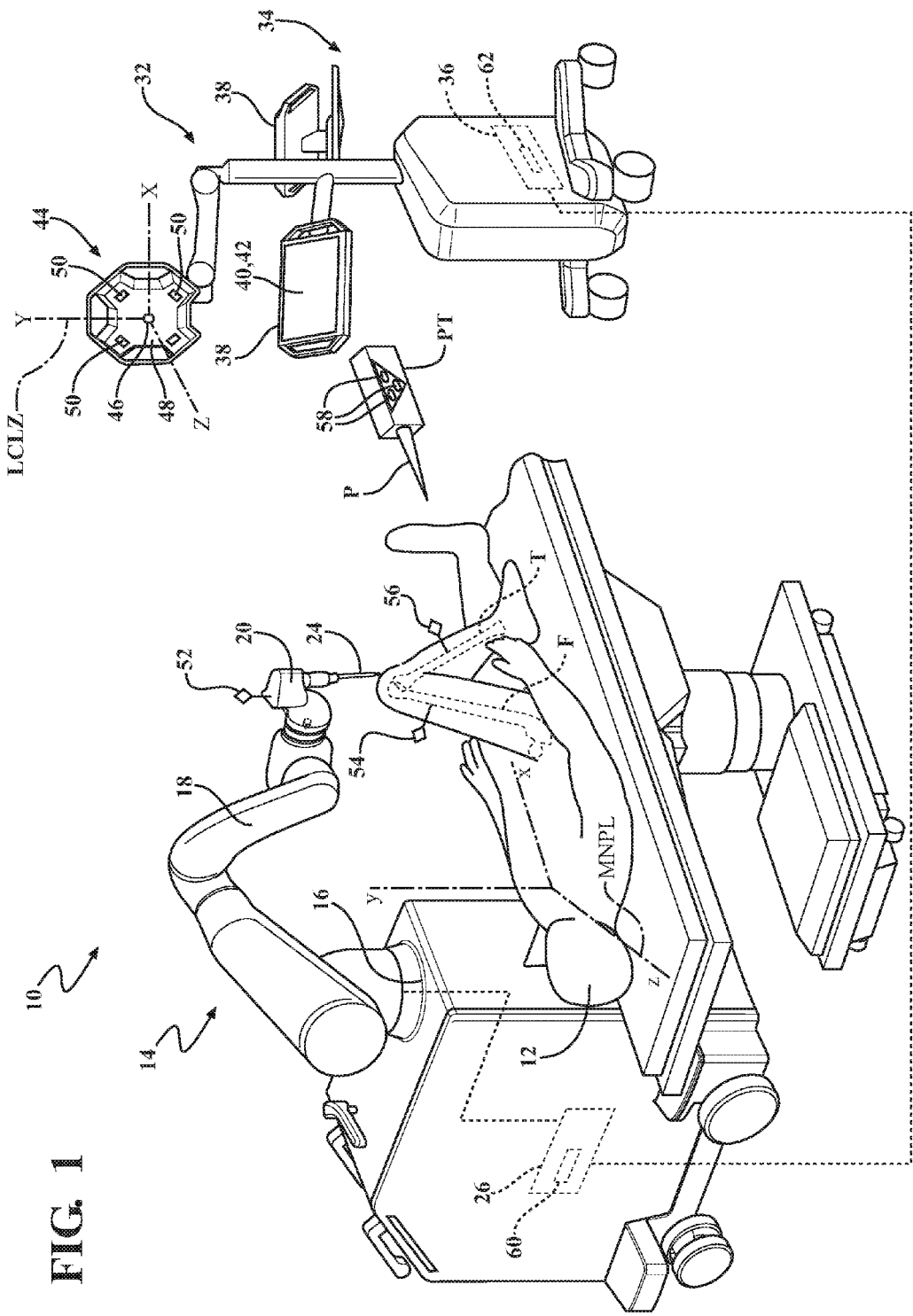
FIG. 1 is a perspective view of a surgical system for manipulating an anatomy of a patient with a tool and demonstrating planned autonomous manipulation of the anatomy according to one embodiment of the invention.

As shown in FIG. 1, the system 10 is a robotic surgical cutting system for cutting away material from the anatomy of the patient 12, such as bone or soft tissue. In FIG. 1, the patient 12 is undergoing a surgical procedure. The anatomy in FIG. 1 includes a femur (F) and a tibia (T) of the patient 12. The surgical procedure may involve tissue removal. In other embodiments, the surgical procedure involves partial or total knee or hip replacement surgery. The system 10 is designed to cut away material to be replaced by surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation," the disclosure of which is hereby incorporated by reference. Those skilled in the art appreciate that the system and method disclosed herein may be used to perform other procedures, surgical or non-surgical, or may be used in industrial applications or other applications where robotic systems are utilized.

The system 10 includes a manipulator 14. The manipulator 14 has a base 16 and a linkage 18. The linkage 18 may comprise links forming a serial arm or parallel arm configuration. An end effector 20 couples to the manipulator 14 and is movable relative to the base 16 to interact with the surgical environment, and more specifically, the anatomy. The end effector 20 is grasped by the operator. One exemplary arrangement of the manipulator 14 and the end effector 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the end effector 20 may be arranged in alternative configurations. The end effector 20 includes an energy applicator 24 designed to contact the tissue of the patient 12 at the surgical site. The end effector 20 may have various configurations depending on the application. The energy applicator 24 may be a drill, a saw blade, a bur, an ultrasonic vibrating tip, a probe, a stylus, or the like. The manipulator 14 also houses a manipulator computer 26, or other type of control unit. The end effector 20 can be like that shown in U.S. Patent Application Publication No. 2014/0276949, filed on Mar. 15, 2014, entitled, "End Effector of a Surgical Robotic Manipulator," which is hereby incorporated by reference.

Figure 2:
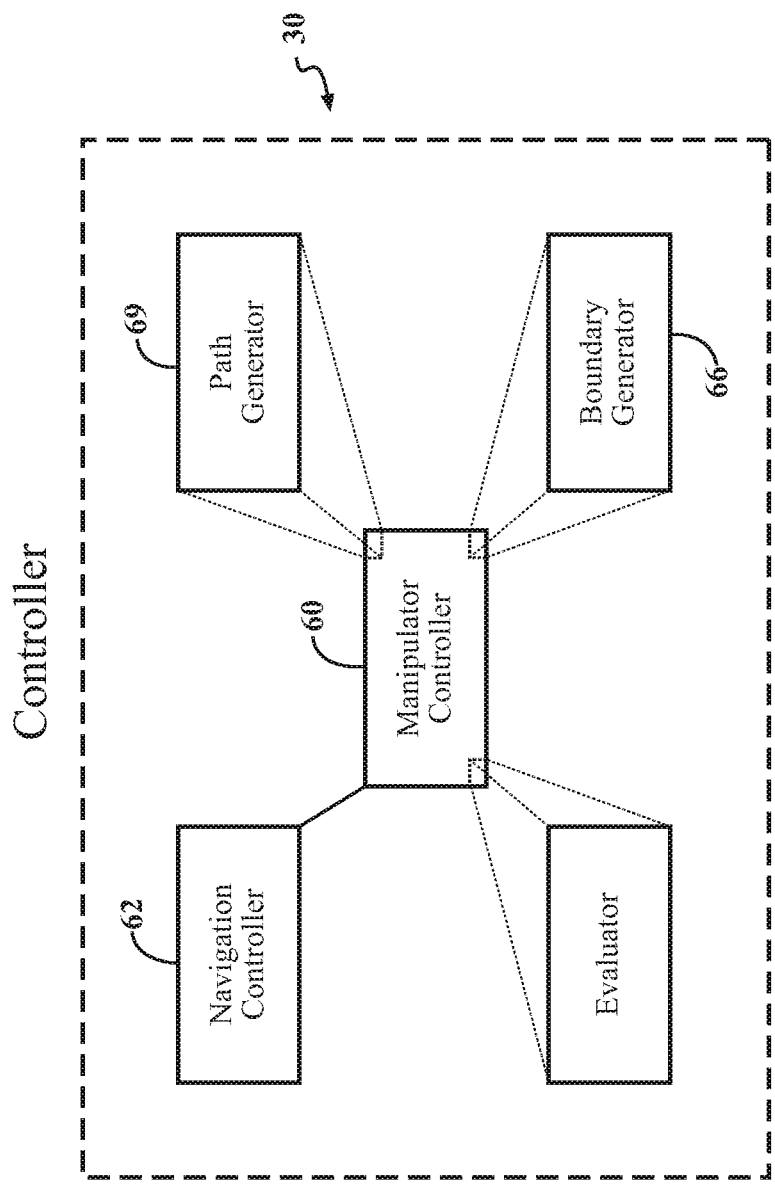
FIG. 2 is a schematic view of a controller for controlling the surgical system according to one embodiment of the invention.

Referring to FIG. 2, the system 10 includes a controller 30. The controller 30 includes software and/or hardware for controlling the manipulator 14. The controller 30 directs the motion of the manipulator 14 and controls an orientation of the end effector 20 with respect to a coordinate system. In one embodiment, the coordinate system is a manipulator coordinate system MNPL (see FIG. 1). The manipulator coordinate system MNPL has an origin, and the origin is located at a point on the manipulator 14. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

The system 10 further includes a navigation system 32. One example of the navigation system 32 and components related thereto is described in U.S. Pat. No. 9,008,757, filed on Sep. 24, 2013, entitled, "Navigation System Including Optical and Non-Optical Sensors," hereby incorporated by reference. The navigation system 32 is set up to track movement of various objects. Such objects include, for example, the end effector 20, and the anatomy, e.g., femur F and tibia T. The navigation system 32 tracks these objects to gather position information of each object in a localizer coordinate system LCLZ. Coordinates in the localizer coordinate system LCLZ may be transformed to the manipulator coordinate system MNPL using conventional transformation techniques. The navigation system 32 is also capable of displaying a virtual representation of their relative positions and orientations to the operator.

The navigation system 32 includes a computer cart assembly 34 that houses a navigation computer 36, and/or other types of control units. A navigation interface is in operative communication with the navigation computer 36. The navigation interface includes one or more displays 38. First and second input devices 40, 42 such as a keyboard and mouse may be used to input information into the navigation computer 36 or otherwise select/control certain characteristics of the navigation computer 36. Other input devices 40, 42 are contemplated including a touch screen (not shown) or voice-activation. The controller 30 may be implemented on any suitable device or devices in the system 10, including, but not limited to, the manipulator computer 26, the navigation computer 36, and any combination thereof.

The navigation system 32 also includes a localizer 44 that communicates with the navigation computer 36. In one embodiment, the localizer 44 is an optical localizer and includes a camera unit 46. The camera unit 46 has an outer casing 48 that houses one or more optical position sensors 50. The system 10 includes one or more trackers. The trackers may include a pointer tracker PT, a tool tracker 52, a first patient tracker 54, and a second patient tracker 56. The trackers include active markers 58. The active markers 58 may be light emitting diodes or LEDs. In other embodiments, the trackers 52, 54, 56 may have passive markers, such as reflectors, which reflect light emitted from the camera unit 46. Those skilled in the art appreciate that the other suitable tracking systems and methods not specifically described herein may be utilized.

In the illustrated embodiment of FIG. 1, the first patient tracker 54 is firmly affixed to the femur F of the patient 12 and the second patient tracker 56 is firmly affixed to the tibia T of the patient 12. The patient trackers 54, 56 are firmly affixed to sections of bone. The tool tracker 52 is firmly attached to the end effector 20. It should be appreciated that the trackers 52, 54, 56 may be fixed to their respective components in any suitable manner.

The trackers 52, 54, 56 communicate with the camera unit 46 to provide position data to the camera unit 46. The camera unit 46 provides the position data of the trackers 52, 54, 56 to the navigation computer 36. In one embodiment, the navigation computer 36 determines and communicates position data of the femur F and tibia T and position data of the end effector 20 to the manipulator computer 26. Position data for the femur F, tibia T, and end effector 20 may be determined by the tracker position data using conventional registration/navigation techniques. The position data includes position information corresponding to the position and/or orientation of the femur F, tibia T, end effector 20 and any other objects being tracked. The position data described herein may be position data, orientation data, or a combination of position data and orientation data.

The manipulator computer 26 transforms the position data from the localizer coordinate system LCLZ into the manipulator coordinate system MNPL by determining a transformation matrix using the navigation-based data for the end effector 20 and encoder-based position data for the end effector 20. Encoders (not shown) located at joints of the manipulator 14 are used to determine the encoder-based position data. The manipulator computer 26 uses the encoders to calculate an encoder-based position and orientation of the end effector 20 in the manipulator coordinate system MNPL. Since the position and orientation of the end effector 20 are also known in the localizer coordinate system LCLZ, the transformation matrix may be generated.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include sets of instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules.

In one embodiment, the controller 30 includes a manipulator controller 60 for processing data to direct motion of the manipulator 14. The manipulator controller 60 may receive and process data from a single source or multiple sources.

The controller 30 further includes a navigation controller 62 for communicating the position data relating to the femur F, tibia T, and end effector 20 to the manipulator controller 60. The manipulator controller 60 receives and processes the position data provided by the navigation controller 62 to direct movement of the manipulator 14. In one embodiment, as shown in FIG. 1, the navigation controller 62 is implemented on the navigation computer 36.

The manipulator controller 60 or navigation controller 62 may also communicate positions of the patient 12 and end effector 20 to the operator by displaying an image of the femur F and/or tibia T and the end effector 20 on the display 38. The manipulator computer 26 or navigation computer 36 may also display instructions or request information on the display 38 such that the operator may interact with the manipulator computer 26 for directing the manipulator 14.

The manipulator 14 autonomously interacts with the anatomy. Specifically, the system 10 may include a semi-autonomous mode, an example of which is described in U.S. Pat. No. 9,119,655, entitled, "Surgical Manipulator Capable of Controlling a Surgical Instrument in Multiple Modes," the disclosure of which is hereby incorporated by reference. In the semi-autonomous mode, the manipulator 14 directs autonomous movement of the end effector 20 and, in turn, the energy applicator 24 at the surgical site. The manipulator 14 is capable of moving the end effector 20 free of operator assistance. Free of operator assistance may mean that an operator does not physically contact the end effector 20 to apply force to move the end effector 20. Instead, the operator may use some form of control to remotely manage starting and stopping of movement. For example, the operator may hold down a button of a remote control to start movement of the end effector 20 and release the button to stop movement of the end effector 20. Alternatively, the operator may press a button to start movement of the end effector 20 and press a button to stop movement of the end effector 20.

Figure 3:
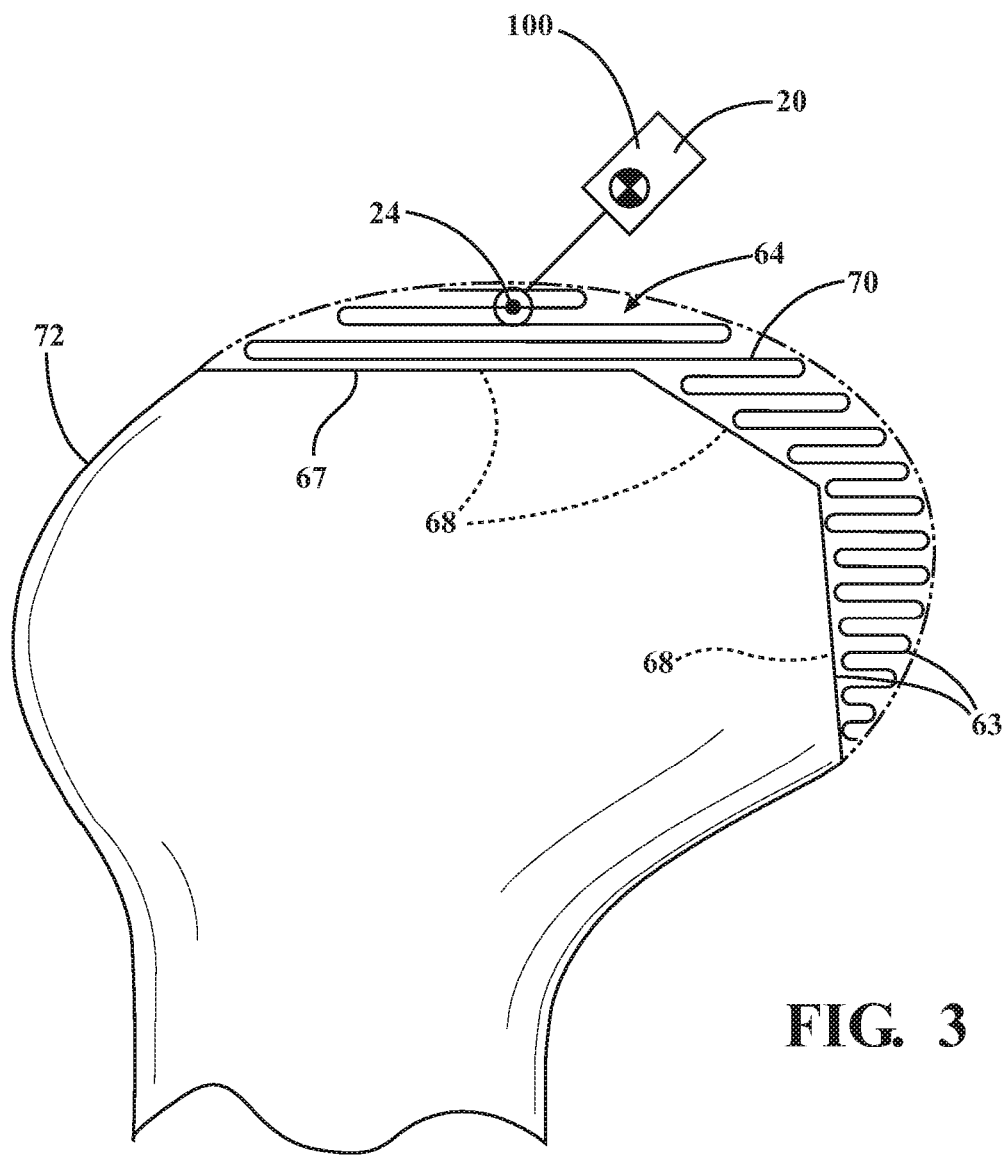
FIG. 3 is a side view of the tool manipulating the anatomy in a first (manipulation) mode according to manipulation parameters according to one example.

The controller 30 is configured to generate manipulation parameters 63 in relation to a volume 64 of the anatomy, as shown in FIG. 3. The manipulation parameters 63 represent planned constraints on autonomous manipulation of the volume 64 by the energy applicator 24 of the end effector 20. As described below, the manipulation parameters 63 may include virtual cutting boundaries, tool cutting paths, or any combination thereof. The manipulation parameters 63 are defined to promote manipulation, removal, and/or cutting of the volume 64 of the anatomy. The manipulation parameters 63 are executed in a first mode. In one embodiment, the first mode may be understood to be a "manipulation" or "cutting" mode. Therefore, for simplicity, the first mode is hereinafter referred to as the manipulation mode in the detailed description.

As shown in FIG. 2, the controller 30 includes a boundary generator 66 for generating the manipulation parameters 63. The boundary generator 66 is a software module that may be implemented on the manipulator controller 60, as shown in FIG. 2. Alternatively, the boundary generator 66 may be implemented on other components, such as the navigation controller 62.

As shown in FIG. 3, the boundary generator 66 generates a cutting boundary 68 for constraining the end effector 20 and/or energy applicator 24 in relation to the anatomy. The cutting boundary 68 is a virtual boundary in that the boundary is not physically present, but rather is implemented by controlling position and movement of the manipulator 14 and the end effector 20. The cutting boundary 68 delineates sections of tissue to be removed by the end effector 20 during the surgery from sections of tissue that are to remain after the surgery. As shown in FIG. 3, the cutting boundary 68 is associated with the anatomy, and more specifically a target surface 67 of the anatomy. The cutting boundary 68 is defined in relation to the target surface 67. The target surface 67 is a contiguous defined surface area of the tissue that is to remain after cutting has completed. For implant procedures, the target surface 67 is the surface of the bone remaining after the removal procedure and is the surface to which the implant is to be mounted. The cutting boundary 68 may have a profile that substantially conforms to the target surface 67.

During the procedure, the cutting boundary 68 may be slightly offset or spaced apart from the target surface 67. In one embodiment, this is done to account for the size and manipulation characteristics of the energy applicator 24 of the end effector 20. The manipulation characteristics of the end effector 20 may cause a breaching of the cutting boundary 68. To account for this overreaching, the cutting boundary 68 may be translated from target surface 67 by a predetermined distance defined between the target surface 67 and the cutting boundary 68. Those skilled in the art understand that the cutting boundary 68 may have other configurations not specifically described herein and may be configured or oriented in relation to the anatomy according to other embodiments not shown or described.

The cutting boundary 68 may be derived from various inputs to the manipulator 14, and more specifically, the boundary generator 66. One input into the boundary generator 66 includes preoperative images of the site on which the procedure is to be performed. If the manipulator 14 selectively removes tissue so the patient 12 may be fitted with an implant, a second input into the boundary generator 66 is a map of the shape of the implant. The initial version of this map may come from an implant database. The shape of the implant defines the boundaries of the tissue that should be removed to receive the implant. This relationship is especially true if the implant is an orthopedic implant intended to be fitted to the bone of the patient 12. Preoperative images of the anatomy may be segmented to create a computer-generated model of the anatomy. The manipulation parameters 63 may be generated based on the computer-generated model of the anatomy. More specifically, the cutting boundary 68 may be generated in relation to the computer-generated model.

Another input into boundary generator 66 is the operator settings. These settings may indicate to which tissue the energy applicator 24 should be applied. If the energy applicator 24 removes tissues, the settings may identify the boundaries between the tissue to be removed and the tissue that remains after application of the energy applicator 24. If the manipulator 14 assists in the fitting of an orthopedic implant, these settings may define where over the tissue the implant should be positioned. These settings may be entered preoperatively using a data processing unit. Alternatively, these settings may be entered through an input/output unit associated with one of the components of the system 10 such as with navigation interface 40, 42.

Based on the above input data and instructions, boundary generator 66 may generate the cutting boundary 68. The cutting boundary 68 may be two-dimensional or three-dimensional. For example, the cutting boundary 68 may be generated as a virtual map or other three-dimensional model. The created maps or models guide movement of the end effector 20. The models may be displayed on displays 38 to show the locations of the objects. Additionally, information relating to the models may be forwarded to the manipulator controller 60 to guide the manipulator 14 and corresponding movement of the end effector 20 relative to the cutting boundary 68.

In practice, prior to the start of the procedure the operator at the surgical site may set an initial version of the cutting boundary 68. At the start of the procedure, data that more precisely defines the implant that is to be actually fitted to the patient 12 may be loaded into the boundary generator 66. Such data may come from a storage device associated with the implant such as a memory stick or an RFID tag. Such data may be a component of the implant database data supplied to the boundary generator 66. These data are based on post manufacture measurements of the specific implant. These data provide a definition of the shape of the specific implant that, due to manufacturing variations, may be slightly different than the previously available stock definition of implant shape. Based on this implant-specific data, the boundary generator 66 may update the cutting boundary 68 to reflect the boundaries between the tissue to be removed and the tissue that should remain in place. Implants that could be implanted into the patient 12 include those shown in U.S. patent application Ser. No. 13/530,927, filed on Jun. 22, 2012 and entitled, "Prosthetic Implant and Method of Implantation", hereby incorporated by reference. The implants disclosed herein could be implanted in the patient 12 after the appropriate amount of material, such as bone, is removed. Other implants are also contemplated.

As shown in FIG. 2, the controller 30 further includes a tool path generator 69 for generating manipulation parameters 63. The tool path generator 69 is another software module run by the controller 30, and more specifically, the manipulator controller 60. The tool path generator 69 generates a cutting path 70 for the end effector 20 to follow, as shown in FIG. 3. The cutting path 70 is represented by the back and forth line. In FIG. 3, the cutting path 70 is configured to facilitate removal of the volume 64 of bone which is to be removed to receive the implant. The smoothness and quality of the finished surface depends in part of the relative positioning of the back and forth line. More specifically, the closer together each back and forth pass of the line, the more precise and smooth is the finished surface. In FIG. 3, the dashed line represents the exterior surface 72 of the bone that is to be removed using manipulator 14. One exemplary system and method for generating the cutting path 70 is explained in U.S. Pat. No. 9,119,655, entitled, "Surgical Manipulator Capable of Controlling a Surgical Instrument in Multiple Modes," the disclosure of which is hereby incorporated by reference.

II. System and Method Overview

As shown in FIGS. 4-10, the system 10 and method are configured to demonstrate planned autonomous manipulation of the anatomy. The system 10 includes a demonstrative tool 100 configured to interact with the anatomy to demonstrate characteristics of the planned manipulation. The controller 30 does so in a second mode. In one embodiment, the second mode may be understood to be a "demo" or "demonstration" mode. Therefore, for simplicity, the second mode is hereinafter referred to as the demo mode in the detailed description. The demonstrative tool 100 interacts with the anatomy to demonstrate the planned procedure in the demo mode. As such, characteristics of the manipulation parameters 63 are visually demonstrated to the operator in the demo mode.

In one embodiment, the demonstrative tool 100 is the end effector 20 itself, and in particular, the energy applicator 24. That is, the end effector 20 is utilized to demonstrate the planned procedure and carry out the planned procedure. Thus, the terms "demonstrative tool" and "end effector" may be interchangeable depending upon if the end effector 20 is also utilized as the demonstrative tool 100, as described in this section. Accordingly, in this section, it is to be understood that the end effector 20 is the demonstrative tool 100 and that the term "demonstrative tool" is recited to help distinguish demonstrative and manipulative characteristics of the system 10 and method.

Figure 4:
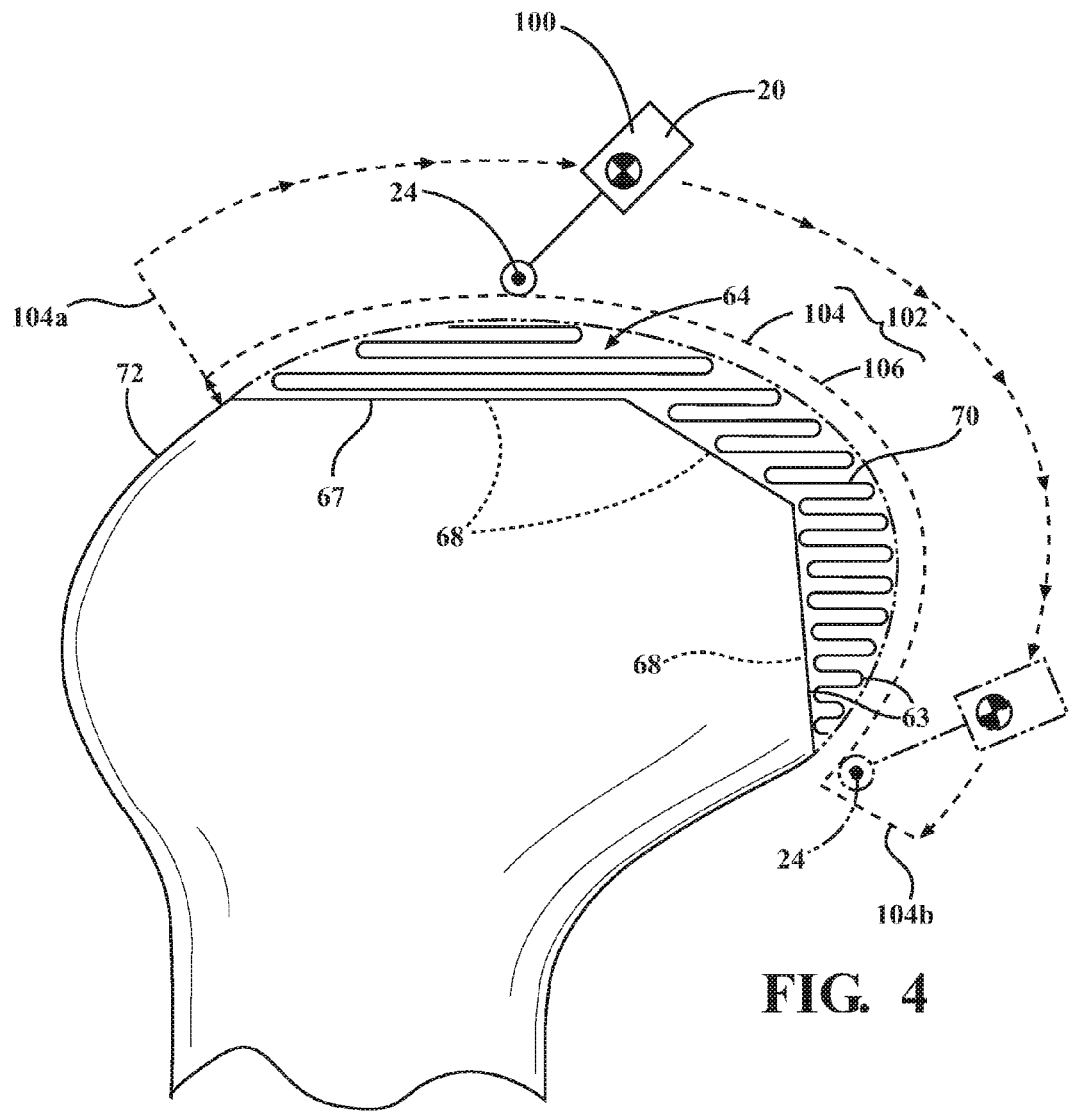
FIG. 4 is a side view of the tool providing a non-invasive demonstration of characteristics of planned manipulation in a second (demo) mode according to one example.

As shown in FIG. 4, the controller 30 generates demonstrative parameters 102 relating to the manipulation parameters 63. The demonstrative parameters 102 represent characteristics of the planned constraints on autonomous manipulation of the volume 64 in the manipulation mode. Movement of the demonstrative tool 100 is dictated and restricted by the demonstrative parameters 102.

The demonstrative parameters 102 are defined in relation to the exterior surface 72 of the anatomy such that the demonstrative parameters 102 are less invasive to the anatomy than the manipulation parameters 63. Unlike the invasiveness of manipulation in the manipulation mode, demonstration in the demo mode is minimally or non-invasive as it is performed in relation to the exterior surface 72 of the anatomy. Those skilled in the art appreciate that demonstration is performed in relation to some characteristics of the manipulation parameters 63 and not based on the exact manipulation parameters 63 because doing so would cause manipulation of the anatomy, thereby defeating one major purpose of providing demonstration.

The controller 30 is configured to instruct movement of the demonstrative tool 100 in accordance with the demonstrative parameters 102. In one embodiment, the controller 30 instructs autonomous movement of the demonstrative tool 100 in the demo mode. That is, movement of the demonstrative tool 100 in accordance with the demonstrative parameters 102 occurs autonomously in the demo mode. Autonomous movement of the demonstrative tool 100 occurs free of operator assistance such that the operator does not physically contact the demonstrative tool 100 to apply force to move the demonstrative tool 100. By autonomously moving the demonstrative tool 100 in the demo mode, the operator may visualize characteristics of the manipulation parameters 63 free of distraction. Details described and incorporated by reference herein regarding autonomous movement of the end effector 20 in the manipulation mode are equally applicable to autonomous movement of the demonstrative tool 100 in the demo mode.

The demonstrative parameters 102 relate to the manipulation parameters 63. The demonstrative parameters 102 may be generated from the same inputs to the manipulator 14 as the inputs utilized in generating the cutting boundary 68 and/or cutting path 70. The boundary generator 66 and tool path generator 69 of the controller 30 may generate the demonstrative parameters 102. The demonstrative parameters 102 may be generated based on the computer-generated model of the anatomy. However, unlike manipulation parameters 63, which promote manipulation of the volume 64, the demonstrative parameters 102 are defined in relation to the exterior surface 72 of the anatomy. The demonstrative parameters 102 significantly preserve the volume 64 because the demonstrative tool 100 is prevented from significantly penetrating the exterior surface 72.

FIG. 4 illustrates one example of the demonstrative parameters 102 wherein the demonstrative parameters 102 are non-invasive. The demonstrative parameters 102 are defined such that the demonstrative tool 100 is spaced apart from the exterior surface 72 of the anatomy throughout movement in the demo mode. That is, the demonstrative tool 100 does not physically touch the exterior surface 72.

As shown in FIGS. 4-9, the demonstrative parameters 102 may include a demonstrative boundary 104, a demonstrative path 106, or any combination thereof. Several examples of the relationship between the demonstrative parameters 102 and the cutting boundary 68 and/or cutting path 70 are described in detail below.

The demonstrative path 106 is derived from the cutting boundary 68 and/or cutting path 70. The demonstrative path 106 demonstrates a representation of the cutting boundary 68 and/or cutting path 70, but does so in relation to the exterior surface 72 of the anatomy. The demonstrative tool 100 moves along the demonstrative path 106 to demonstrate the cutting boundary 68 and/or cutting path 70 in the demo mode. The demonstrative path 106 is spaced apart from the cutting boundary 68 and cutting path 70.

Figure 7:
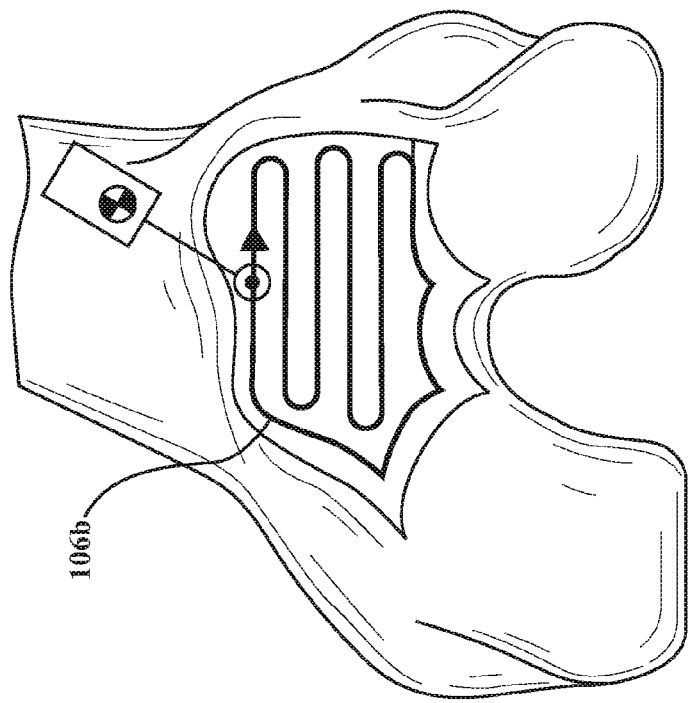
FIG. 7 is a perspective view of the tool providing the demonstration according to the demonstrative boundary and the demonstrative path for a patellofemoral implant procedure according to one example.
Figure 6:
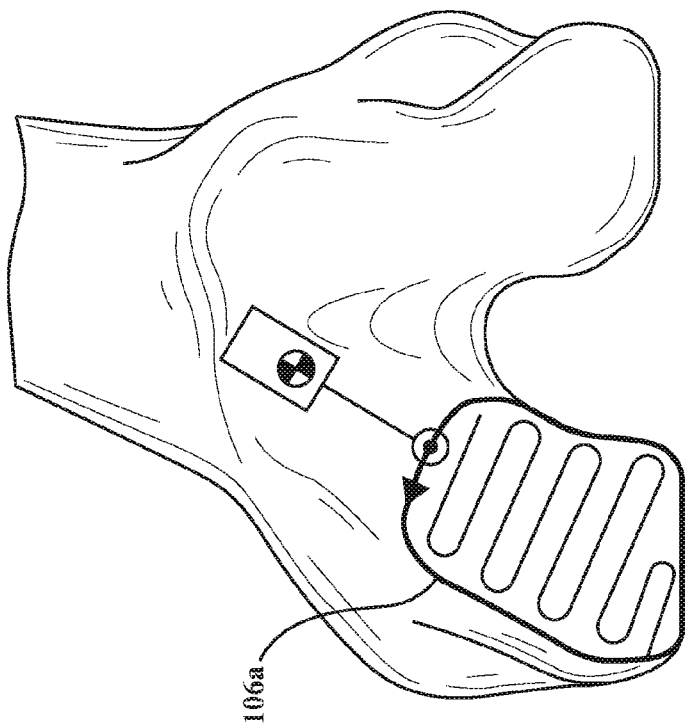
FIG. 6 is a perspective view of the tool providing the demonstration according to a demonstrative boundary and a demonstrative path tailored for a femoral medial implant procedure according to one example.

FIG. 6 illustrates a perspective view of the anatomy of FIG. 4, which is a femur bone requiring a medial implant in a partial (unicompartmental) knee replacement procedure. FIG. 7 illustrates another perspective view of a femur bone, this time requiring a patellofemoral implant. In both FIG. 6 and FIG. 7, the demonstrative path 106 is specifically tailored to the implant location. In FIG. 6, the demonstrative path 106a represents the perimeter of the underlying cutting boundary 68. In FIG. 7, the demonstrative path 106b represents the underlying cutting path 70. Again, the demonstrative path 106 may represent both the underlying cutting boundary 68 and cutting path 70.

The demonstrative tool 100 traverses along the demonstrative path 106 in the demo mode. Generally, the demonstrative tool 100 traverses along the demonstrative path 106 at least once, and potentially, as many times as desired by the operator.

The demonstrative boundary 104 constrains movement of the demonstrative tool 100 such that the demonstrative tool 100 is prevented from moving beyond a virtual constraint defined by the demonstrative boundary 104. The virtual constraint may align with the perimeter derived from the cutting boundary 68 and/or cutting path 70. The demonstrative tool 100 moves in relation to the virtual constraint to demonstrate the perimeter in the demo mode. The demonstrative boundary 104 identifies to the operator the limits of the cutting boundary 68, but in relation to the exterior surface 72 of the anatomy. The demonstrative boundary 104 encompasses the demonstrative path 106 or extends beyond the demonstrative path 106. The demonstrative boundary 104 may also be tailored to the specific implant.

In some instances, the demonstrative boundary 104 supplements the demonstrative path 106. For example, the demonstrative tool 100 may move along the demonstrative path 106 to demonstrate the perimeter. The demonstrative boundary 104 prevents the demonstrative tool 100 from inadvertently approaching or touching the exterior surface 72. This may be particularly advantageous in instances when the patient (anatomy) moves or movement of the demonstrative tool 100 is otherwise interfered with during demonstration. This may also be advantageous when the operator wishes to manually confirm the limits the underlying cutting boundary 68 with the demonstrative tool 100. For example, the operator may manually move the demonstrative tool 100 against the demonstrative boundary 104 to haptically sense the presence of the demonstrative boundary 104. The operator may perform such technique before activating demonstration in the demo mode.

In other examples, the demonstrative path 106 can be actively controlled and/or manipulated by the operator. The demonstrative path 106 may be reactively employed in response to sensed movement of the tool 100 by the operator. For example, the tool 100 may initially be moved along the demonstrative boundary 104. Thereafter, the operator may desire to move the tool 100 to the demonstrative path 106 by moving the tool 100 away from the boundary 104 and towards the primary cutting area of the surgical site. In such instances, the demonstrative path 106 reactively triggers such that the tool 100 becomes locked into the demonstrative path 106.

In one embodiment, the demonstrative boundary 104 is spaced apart from the cutting boundary 68 such that the exterior surface 72 is located between the target surface 67 and the demonstrative boundary 104. By controlling movement of the demonstrative tool 100 in relation to the exterior surface 72 of the anatomy, the demonstrative boundary 104 prevents the demonstrative tool 100 from reaching the target surface 67, and in some instances, the exterior surface 72. The demonstrative boundary 104 may be spaced apart from the cutting boundary 68 by any distance suitable to provide demonstration.

Figure 8:
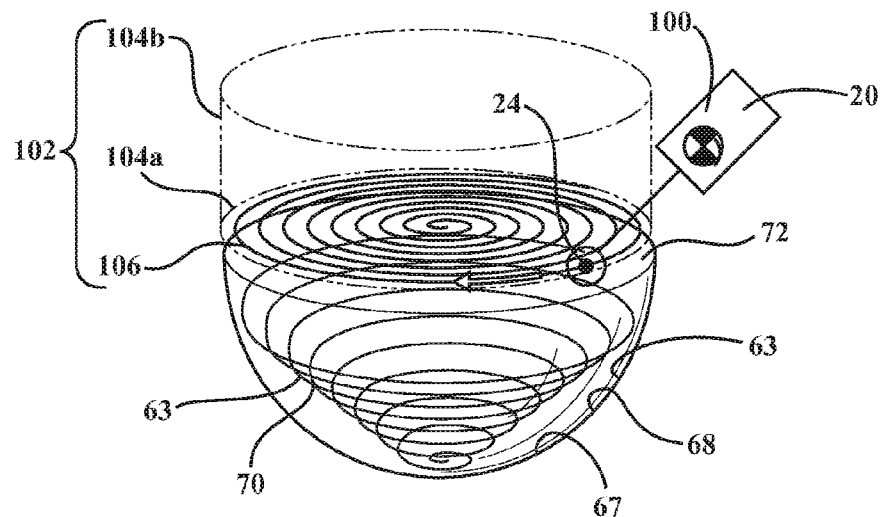
FIG. 8 illustrates the relationship between the manipulation parameters and the demonstrative parameters for a semi-spherical volume.

FIG. 8 provides one example illustrating the relationship between the manipulation parameters 63 and the demonstrative parameters 102. In this example, the cutting boundary 68 and the target surface 67 correspond to the curved surface area of the volume. The cutting path 70 is defined in relation to several layers of the semi-spherical volume. For simplicity in illustration, the cutting path 70 is shown as a multi-layer spiral. The upper flat surface of the volume corresponds to the existing exterior surface 72 of the anatomy prior to cutting or manipulation in the manipulation mode. In this example, the demonstrative path 106 represents a two-dimensional version of the underlying semi-spherical cutting boundary 68 and/or cutting path 70. Thus, the demonstrative path 106 is a two-dimensional spiral corresponding to the underlying three-dimensional cutting path 70. Although flattened, the demonstrative path 106 in this example nevertheless represents significant portions of the intended cutting boundary 68 and/or cutting path 70 with respect to the volume. The demonstrative path 106 may include duplicative movement of the demonstrative tool 100 since the three-dimensional cutting path 70 is flattened into a two-dimensional demonstrative path 106. The demonstrative boundary 104 supplements the demonstrative path 106 by preventing manual movement of the demonstrative tool 100 beyond the virtual constraint defined by the demonstrative boundary 104. In this example, the demonstrative boundaries 104 include a circular disc 104a and a cylindrical wall 104b encompassing the demonstrative path 106. As shown in FIG. 8, the demonstrative boundaries 104 form an open cylindrical volume such that the demonstrative tool 100 is not constrained and free to move upward and away from the volume. However, the demonstrative boundaries 104 may be a closed area or volume such that the demonstrative tool 100 is constrained within the area or volume. The demonstrative boundaries 104 may fill in space within the demonstrative path 106 and may expand beyond the demonstrative path 106.

Figure 9:
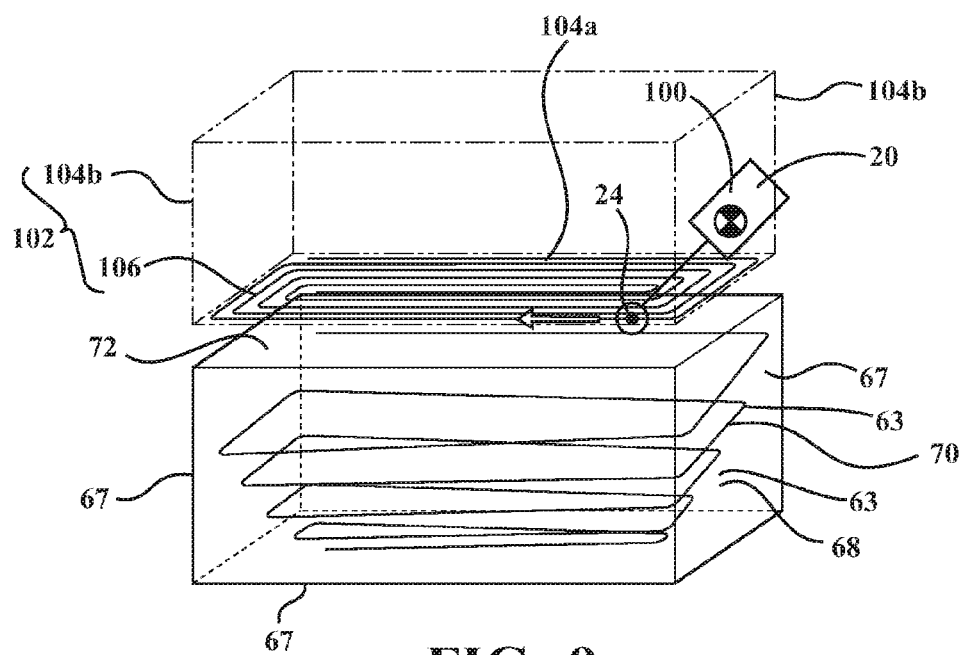
FIG. 9 illustrates the relationship between the manipulation parameters and the demonstrative parameters for a rectangular volume.

FIG. 9 provides another example, this time relating to a rectangular volume of material to be removed. The cutting boundary 68 and the target surface 67 correspond to the interior sides of the rectangular volume. The cutting path 70 is defined in relation to several layers of the rectangular volume. For simplicity in illustration, the cutting path 70 is a multi-layered rectangular spiral. The top surface of the volume corresponds to the existing exterior surface 72 of the anatomy prior to cutting or manipulation in the manipulation mode. In this example, the demonstrative path 106 represents a two-dimensional version of the underlying rectangular cutting boundary 68 and/or cutting path 70. Thus, the demonstrative path 106 is a flattened rectangular spiral. The demonstrative boundary 104 supplements the demonstrative path 106 to prevent manual movement of the demonstrative tool 100 beyond the virtual constraints defined by the demonstrative boundary 104. In this example, the demonstrative boundaries 104 are the sidewalls 104b and the rectangular area 104a encompassing the demonstrative path 106. The demonstrative boundaries 104 may be closed or open areas or volumes.

Similarly, the cutting boundary 68 in FIG. 4 defines a shape designed to receive an implant and the cutting path 70 in FIG. 4 is defined in relation to several layers of the volume 64 for manipulating the anatomy to receive the implant. The demonstrative path 106 is shaped to conform and/or align to the exterior surface 72 of the anatomy and the demonstrative path 106 demonstrates the limits of the underlying cutting boundary 68 and/or cutting path 70. Although not penetrating the exterior surface 72, the demonstrative path 106 in FIG. 4 nevertheless represents the perimeter of the cutting boundary 68. The demonstrative boundary 104 supplements the demonstrative path 106 to prevent manual movement of the demonstrative tool 100 beyond the virtual constraints. In this example, the demonstrative boundaries 104 are the sidewalls 104a, 104b defining the bounds of the underlying cutting boundary 68 and/or cutting path 70.

Figure 10:
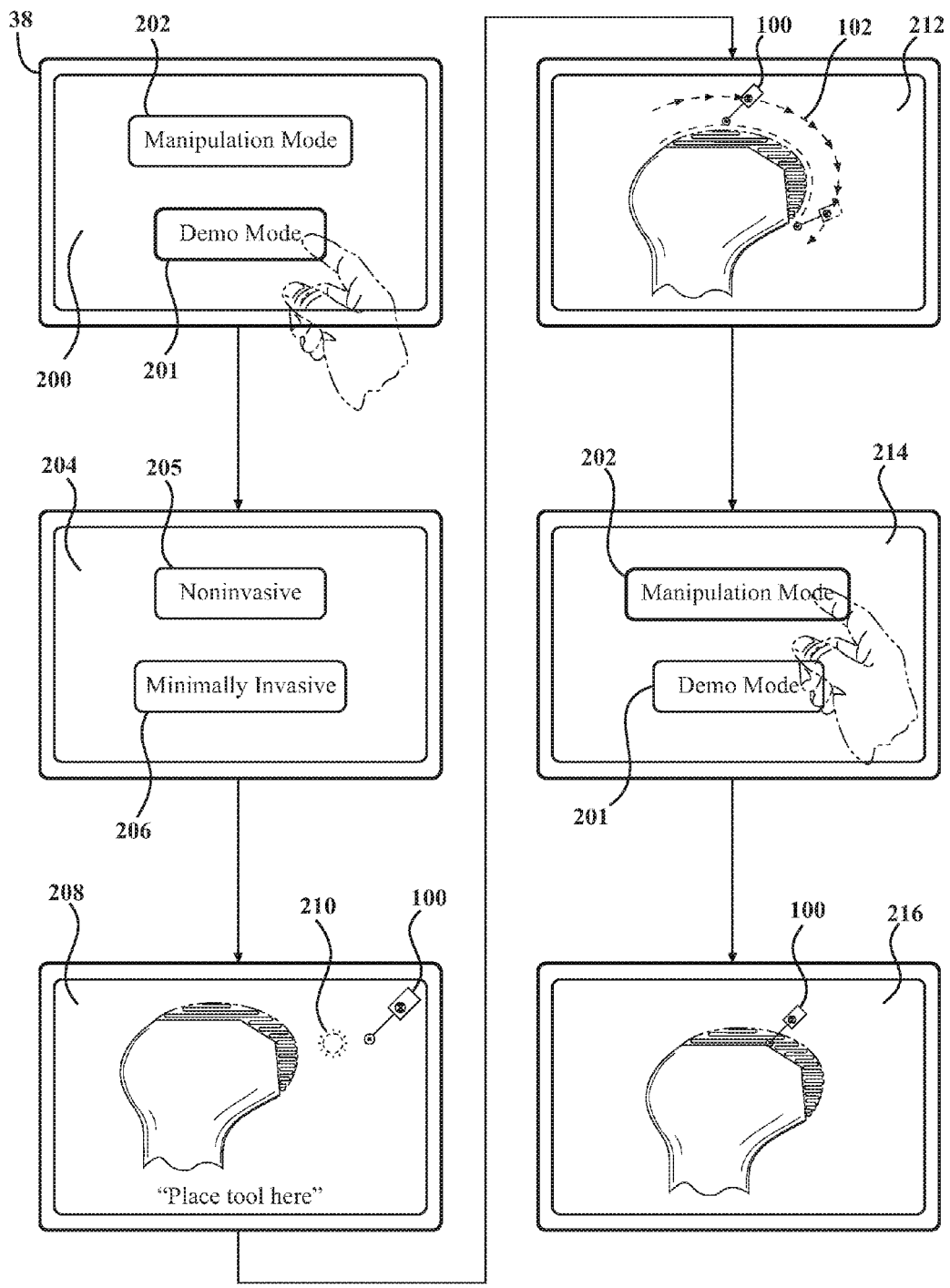
FIG. 10 illustrates a sequential series of screen-shots representing selection and performance of the first (manipulation) mode and second (demo) mode.

FIG. 10 illustrates a series of screen-shots of a display, such as the display 38 of the navigation interface, representing how the operator may utilize the demo mode in relation to the manipulation mode. At screen 200, the display 38 prompts the user to select between the demo mode and the manipulation mode. The demo mode may be selected by pressing a demo mode button 201 and the manipulation mode may be selected by pressing a manipulation mode button 202. The system 10 includes switches or buttons implemented in any suitable hardware or software for allowing the operator to switch between the manipulation mode and demo mode. Here, the operator selects the demo mode by pressing the demo mode button 201.

At screen 204, the display prompts a demo mode selection screen in response to the operator pressing the demo mode button 201. Here, the operator may select a "non-invasive" demo wherein the demonstrative tool 100 does not physically touch the exterior surface 72 during demonstration or a "minimally invasive" demo wherein the demonstrative tool 100 grazes, skims or etches the exterior surface 72 during demonstration. This type of demo is described in detail below. The "non-invasive" demo mode may be selected by pressing a "non-invasive" demo mode button 205 and the "minimally invasive" demo mode may be selected by pressing a "minimally invasive" mode button 206.

At screen 208, the display shows the demonstrative tool 100 in relation to the anatomy, as shown and described in FIG. 3, for example. The system 10 tracks the anatomy and the demonstrative tool 100 in real-time and displays the positions of the anatomy and the demonstrative tool 100 relative to one another. Here, the system 10 creates a demo initiation region 210 for ensuring that the demonstrative tool 100 is in a suitable position before the demo mode activates. The location of the demo initiation region 210 may be selected based on any suitable factor, such as manipulation parameters 63 or demonstrative parameters 102. The system 10 displays the demo initiation region 210 on the screen with a request for the operator to move the demonstrative tool 100 within the demo initiation region 210. In FIG. 10, the request is textual message stating, "place tool here." The demo initiation region 210 is a virtual region defined with respect to the anatomy. The manipulator 14 may be instructed to stop moving once the system 10 determines that the demonstrative tool 100 enters the demo initiation region 210. Alternatively, the demo initiation region 210 may be a virtual constraint region such that once the demonstrative tool 100 enters the demo initiation region 210, the demo initiation region 210 locks the demonstrative tool 100 in place. Once the demonstrative tool 100 enters the demo initiation region 210, the system 10 is ready to initiate the non-invasive demo mode. In some embodiments, the system 10 may provide a haptic, visual, or audible indicator that the system 10 is ready to initiate the non-invasive demo mode. For example, the system 10 may illuminate a green colored indictor when the once the demonstrative tool 100 enters the demo initiation region 210.

At screen 212, the display shows the demonstrative tool 100 providing the non-invasive demo according to the example of FIG. 4, for example. Movement of the demonstrative tool 100 in the demo mode may be tracked with the navigation system 32. The navigation system 32 tracks the demonstrative tool 100 and displays the virtual representation of the demonstrative tool 100 relative to the position of the anatomy. The manipulator controller 60 or navigation controller 62 may display an image of the femur F and/or tibia T and the demonstrative tool 100 on the display 38.

The system 10 moves the demonstrative tool 100 in accordance with the non-invasive demonstrative parameters 102. The system 10 may present the demo on the display before, after, or simultaneously during actual performance of the demonstration in the demo mode. The operator visually confirms that the intended planned autonomous manipulation of the anatomy, as demonstrated, is satisfactory. The operator may do so by examining the actual, in-person, relationship between the demonstrative tool 100 and the anatomy. Additionally or alternatively, the operator may examine the display 38 presenting the virtual relationship between the demonstrative tool 100 and the anatomy.

Through this process, the demo mode provides operators with a greater sense of control and confidence, thereby alleviating operator hesitancy in using autonomous manipulation in the manipulation mode.

The demo mode may be performed for a predetermined duration or until the operator manually stops the demo mode. Once the demo mode is completed, the demonstrative tool 100 returns to any appropriate position, such as the demo initiation region 210 or a position that is far from the anatomy. At this point, the system 10 may once again prompt the user to select between the demo mode and the manipulation mode at screen 214. Of course, the operator, if desired, may choose to re-experience the demo mode by selecting the demo mode button 201 again. However, if the demo is satisfactory, the operator chooses the manipulation mode button 202 to initiate the manipulation mode. The operator switches from the demo mode to the manipulation mode to activate autonomous manipulation of the anatomy in accordance with the manipulation parameters 63, as described herein. Manipulation in the manipulation mode is displayed in real-time at screen 216.

III. Other Embodiments

The surgical system 10 may implement various other embodiments of the demonstrative tool 100 and demonstrative parameters 102 other than those described above.

In some embodiments, the demonstrative parameters 102 may be mathematically transformed from the manipulation parameters 63. For example, the demonstrative boundary 104 may be derived from the cutting boundary 68. The demonstrative boundary 104 may be shifted apart from the cutting boundary 68 and modified to correspond to the exterior surface 72 of the anatomy. The demonstrative boundary 104 may be formed based on preoperative images of the exterior surface 72 and/or the implant. For example, the demonstrative boundary 104 may be generated as a virtual map or other three-dimensional model.

Similarly, the demonstrative path 106 may be derived from the cutting path 70. The demonstrative path 106 may be spaced apart from the cutting path 70 and transformed to conform to the exterior surface 72 of the anatomy and/or implant. The demonstrative boundary 104 and demonstrative path 106 may be two-dimensional or three-dimensional.

With autonomous movement, there generally is a trade-off between accuracy in movement of the end effector 20 and velocity (feed-rate) of the end effector 20. It may be desirable for operators to quickly execute demonstration in the demo mode such that there is not undue delay in the surgical procedure. To avoid such delay, the demonstrative parameters 102 may be deliberately less accurate than the manipulation parameters 63. For example, the demonstrative boundary 104 may be roughly based on the exterior surface 72. The demonstrative boundary 104 need not be exactly shaped to the exterior surface 72 of the anatomy. For example, the demonstrative boundary 104 may be planar and spaced in relation to a highest point on the exterior surface 72 of the anatomy. The demonstrative boundary 104 need not have the same level of accuracy as the cutting boundary 68 because demonstration may be intended to serve as a check on the manipulation parameters 63. Accuracy may also be diminished because the demonstrative boundary 104 is less invasive than the cutting boundary 68.

Similarly, the demonstrative path 106 may be roughly based on cutting path 70. For example, spacing between the back and forth lines in the cutting path 70 may be increased for the demonstrative path 106 such that less time is required for the demonstrative tool 100 to traverse the path 106.

Figure 5:
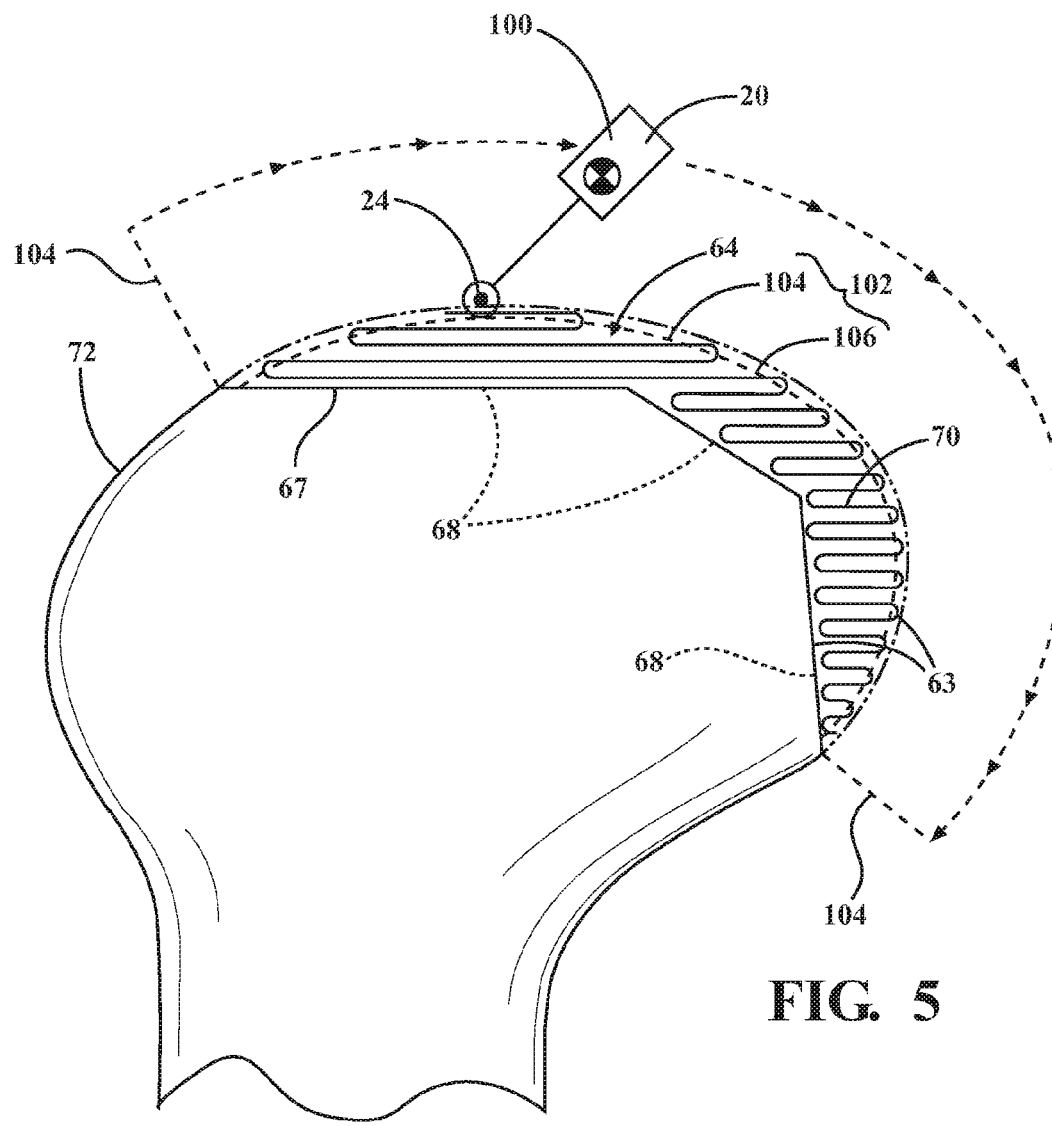
FIG. 5 is a side view of the tool providing a minimally-invasive demonstration of characteristics of planned manipulation in the second (demo) mode according to another example.

In one embodiment, as shown in FIG. 5 for example, the demonstrative parameters 102 may be minimally-invasive, rather than non-invasive. Here, the demonstrative tool 100 may physically manipulate the anatomy in the demo mode during demonstration. The demonstrative parameters 102 are defined such that the demonstrative tool 100 penetrates the exterior surface 72 of the anatomy during movement in the demo mode. The demonstrative tool 100 may graze, scratch, or etch the exterior surface 72 to represent planned cutting boundaries and/or cutting paths. In one embodiment, the demonstrative tool 100 is instructed to graze, scratch, or etch 2 mm or less of the exterior surface 72. In another embodiment, the demonstrative tool 100 is instructed to graze, scratch, or etch 1 mm or less of the exterior surface 72. In yet another embodiment, the demonstrative tool 100 is instructed to graze, scratch, or etch 0.5 mm or less of the exterior surface 72. Placement of the demonstrative boundary 104 beneath the exterior surface 72 in FIG. 5 is exaggerated for simplicity in illustration.

Demonstrative manipulation provides permanent visualization of characteristics of the planned manipulation parameters 63. This way, the operator may physically see a static outline or path representing characteristics of the manipulation parameters 63 after movement ceases in the demo mode. As compared with the manipulation mode, allowing some manipulation in the demo mode is not intended to promote removal of the volume 64 for purposes of reaching the target surface 67 of the anatomy, as intended in the manipulation mode.

FIG. 5 illustrates one implementation of the embodiment wherein the demonstrative parameters 102 are minimally-invasive. The demonstrative parameters 102 are defined such that the demonstrative tool 100 scratches the exterior surface 72 of the anatomy during movement in the demo mode. The demonstrative tool 100 physically touches the exterior surface 72. The demonstrative boundary 104 remains significantly spaced apart from the cutting boundary 68. However, the demonstrative boundary 104 is defined just below the exterior surface 72 such that the demonstrative boundary 104 is located between the cutting boundary 68 and the exterior surface 72. By being just below the exterior surface 72, the demonstrative boundary 104 allows minimal penetration of the exterior surface 72. The demonstrative boundary 104 prevents the demonstrative tool 100 from reaching the target surface 67 and significant portions of the volume 64. The demonstrative boundary 104 may be disposed beneath the exterior surface 72 by any minimally-invasive distance suitable for demonstration.

In some embodiments, the end effector 20 and the demonstrative tool 100 are distinct and separate tools. That is, the demonstrative tool 100 is utilized only for demonstration in the demo mode, and not for manipulation in the manipulation mode. Similarly, the end effector 20 is utilized only for manipulation in the manipulation mode, and not for demonstration in the demo mode. One example of the demonstrative tool 100 may be a stylus or probe for pointing at the anatomy. The demonstrative tool 100 may be supported directly or indirectly by the manipulator 14. Alternatively, the demonstrative tool 100 may be supported and controlled independent of the manipulator 14. When the end effector 20 and the demonstrative tool 100 are distinct and separate tools, details described and incorporated by reference herein regarding the system 10 interactions and control of the end effector 20 are equally applicable to the demonstrative tool 100.

In such instances, the end effector 20 may be swapped out with the demonstrative tool 100 before demonstration is to occur in the demo mode. Thereafter, the demonstrative tool 100 may be swapped with the end effector 20 before manipulation is to occur in the manipulation mode. In embodiments where the demonstrative tool 100 is independently supported, the demonstrative tool 100 may not need to be swapped with the end effector 20 when switching between the manipulation mode and demo mode.

When the end effector 20 serves as the demonstrative tool 100, it may be desirable to ensure that the manipulative capabilities of the end effector 20 are disabled throughout a portion, or the entirety, of the demo mode. For example, disabling the manipulative capabilities of the end effector 20 may include preventing a burr from rotating, and the like. Doing so prevents inadvertent manipulation of the anatomy during demonstration in the demo mode. When the demo mode is switched to the manipulation mode, the manipulative capabilities of the end effector 20 may be enabled to allow the end effector 20 to effectively manipulate the anatomy in the manipulation mode, as intended.

Demonstrating the invasive depth of the planned manipulation in the manipulation mode using the demonstrative tool 100 may be difficult since movement of the demonstrative tool 100 is non-invasive or minimally-invasive. As such, the navigation system 32 may supplement autonomous demonstration in the demo mode. The navigation system 32 may provide a heat map with respect to the virtual representation of the exterior surface 72 of the anatomy provided on the display 38. The heat map may be based on the manipulation parameters 63 and may present different colors to fully capture the invasive depth of the manipulation parameters 63. For example, darker colors may indicate deeper planned cutting boundaries 68 or paths 70 while lighter colors indicate shallower cutting boundaries 68 or paths 70. Movement of the demonstrative tool 100 may be layered over the heat map to give the operator a full demonstrative effect.

In some embodiments, the demonstrative parameters 102 may be illuminated directly onto the exterior surface 72 in the demo mode during movement of the demonstrative tool 100. This may be done to supplement demonstration. For example, the demonstrative boundary 104 or demonstrative path 106 may be illuminated on the exterior surface 72 of the anatomy using an illuminated point source or line. The point source or line may be static or moving (animated). For example, when animated, the point source or line may create a comet tail traversing the demonstrative boundary 104 or demonstrative path 106. The system 10 may employ any suitable illumination device, such as a laser or projector, for illuminating the demonstrative parameters 102 directly onto the exterior surface 72 in the demo mode.

The system 10 may provide options for modifying settings relating to demonstration in the demo mode. This option may be set in the operator settings. Such settings may dictate when, where, and how to provide the demonstration. For example, the operator may set whether switching between the manipulation mode and the demo mode is performed manually or autonomously. The operator may also set whether the demonstration is to be performed by the end effector 20 or some other demonstrative tool 100, such as a probe, stylus, etc. The operator may set the speed and/or accuracy of the demonstration. For example, the operator may set the speed of the demo to be faster than manipulation if the demo is non-invasive or slower than manipulation if the demo is minimally invasive. The operator may set whether to enable or disable the certain characteristics of the demonstration, such as the demonstrative boundary 104 or demonstrative path 106. Moreover, the operator may disable demonstration altogether. Those skilled in the art appreciate that various other settings are possible in relation to modifying the demonstration that are not specifically recited herein.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A robotic surgical system for manipulating an anatomy and demonstrating planned autonomous manipulation of the anatomy, said system comprising:
an end effector being configured to manipulate the anatomy;
a demonstrative tool being configured to interact with the anatomy;
a controller configured to generate manipulation parameters representing planned constraints on autonomous manipulation of a volume of the anatomy by said end effector in a first mode and generate demonstrative parameters relating to said manipulation parameters and defined in relation to a surface of the anatomy such that said demonstrative parameters are less invasive to the anatomy than said manipulation parameters and wherein said controller is configured to instruct movement of said demonstrative tool in accordance with said demonstrative parameters in a second mode thereby demonstrating planned constraints on autonomous manipulation of the anatomy in relation to the surface of the anatomy.

2. The robotic surgical system of claim 1 wherein said demonstrative tool is configured to manipulate the anatomy.

3. The robotic surgical system of claim 2 wherein said demonstrative parameters are defined such that said demonstrative tool penetrates the surface of the anatomy during movement in said second mode.

4. The robotic surgical system of claim 1 wherein said demonstrative parameters are non-invasive.

5. The robotic surgical system of claim 4 wherein said demonstrative parameters are defined such that said demonstrative tool is spaced apart from the surface of the anatomy throughout movement in said second mode.

6. The robotic surgical system of claim 1 wherein said end effector is configured to cut bone.

7. The robotic surgical system of claim 1 wherein said manipulation parameters define a cutting boundary in relation to the volume of the anatomy and wherein said demonstrative parameters define a demonstrative boundary relating to said cutting boundary.

8. The robotic surgical system of claim 1 wherein said manipulation parameters define a cutting path in relation to the volume of the anatomy and wherein said demonstrative parameters define a demonstrative path relating to said cutting path.

9. A method of demonstrating planned autonomous manipulation of an anatomy by an end effector of a robotic surgical system, said method comprising:
generating manipulation parameters representing planned constraints on autonomous manipulation of a volume of the anatomy by the end effector in a first mode;
generating demonstrative parameters relating to the manipulation parameters and defined in relation to a surface of the anatomy such that the demonstrative parameters are less invasive to the anatomy than the manipulation parameters; and
moving a demonstrative tool in accordance with the demonstrative parameters in a second mode thereby demonstrating planned constraints on autonomous manipulation of the anatomy in relation to the surface of the anatomy.

10. The method of claim 9 further including the step of producing a computer-generated model of the anatomy.

11. The method of claim 10 wherein the step of generating manipulation parameters includes generating the manipulation parameters based on the computer-generated model of the anatomy.

12. The method of claim 10 wherein the step of generating demonstrative parameters includes generating the demonstrative parameters based on the computer-generated model of the anatomy.

13. The method of claim 9 wherein the step of moving the demonstrative tool includes causing the demonstrative tool to remain spaced apart from the surface of the anatomy throughout movement in the second mode.

14. The method of claim 9 wherein the step of moving the demonstrative tool includes causing the demonstrative tool to penetrate the surface of the anatomy during movement in the second mode.

15. The method of claim 9 further including the step of switching between the second mode and the first mode.

16. The method of claim 15 further including the step of moving the end effector in accordance with the manipulation parameters to manipulate the anatomy in the first mode after switching from the second mode to the first mode.

17. A robotic surgical system for manipulating an anatomy and demonstrating planned autonomous manipulation of the anatomy, said system comprising:
a tool being configured to manipulate the anatomy;
a controller configured to generate manipulation parameters representing planned constraints on autonomous manipulation of a volume of the anatomy by said tool in a first mode and generate demonstrative parameters relating to said manipulation parameters and defined in relation to a surface of the anatomy such that said demonstrative parameters are less invasive to the anatomy than said manipulation parameters and wherein said controller is configured to instruct movement of said tool in accordance with said demonstrative parameters in a second mode thereby demonstrating planned constraints on autonomous manipulation of the anatomy in relation to the surface of the anatomy.

18. The robotic surgical system of claim 17 wherein said demonstrative parameters are defined such that said tool penetrates the surface of the anatomy during movement in said second mode.

19. The robotic surgical system of claim 17 wherein said demonstrative parameters are non-invasive.

20. The robotic surgical system of claim 19 wherein said demonstrative parameters are defined such that said tool is spaced apart from the surface of the anatomy throughout movement in said second mode.

21. The robotic surgical system of claim 17 wherein said tool is configured to cut bone.

22. The robotic surgical system of claim 17 wherein said manipulation parameters define a cutting boundary in relation to the volume of the anatomy and wherein said demonstrative parameters define a demonstrative boundary relating to said cutting boundary.

23. The robotic surgical system of claim 17 wherein said manipulation parameters define a cutting path in relation to the volume of the anatomy and wherein said demonstrative parameters define a demonstrative path relating to said cutting path.

24. A method of demonstrating planned autonomous manipulation of an anatomy by a tool of a robotic surgical system, said method comprising:
generating manipulation parameters representing planned constraints on autonomous manipulation of a volume of the anatomy by the tool in a first mode;

generating demonstrative parameters relating to the manipulation parameters and defined in relation to a surface of the anatomy such that the demonstrative parameters are less invasive to the anatomy than the manipulation parameters; and moving the tool in accordance with the demonstrative parameters in a second mode thereby demonstrating planned constraints on autonomous manipulation of the anatomy in relation to the surface of the anatomy.

25. The method of claim 24 further including the step of electrically activating manipulative capabilities of the tool in the first mode and electrically deactivating manipulative capabilities of the tool in the second mode.

26. The method of claim 24 further including the step of producing a computer-generated model of the anatomy.

27. The method of claim 26 wherein the step of generating manipulation parameters includes generating the manipulation parameters based on the computer-generated model of the anatomy.

28. The method of claim 24 wherein the step of generating demonstrative parameters includes generating the demonstrative parameters based on the computer-generated model of the anatomy.

29. The method of claim 24 wherein the step of moving the tool includes causing the tool to remain spaced apart from the surface of the anatomy throughout movement in the second mode.

30. The method of claim 24 wherein the step of moving the tool includes causing the tool to penetrate the surface of the anatomy during movement in the second mode.

31. The method of claim 24 further including the step of switching between the second mode and the first mode.

32. The method of claim 24 further including the step of moving the tool in accordance with the manipulation parameters to manipulate the anatomy in the first mode after switching from the second mode to the first mode.

* * * * *